Figure 1:
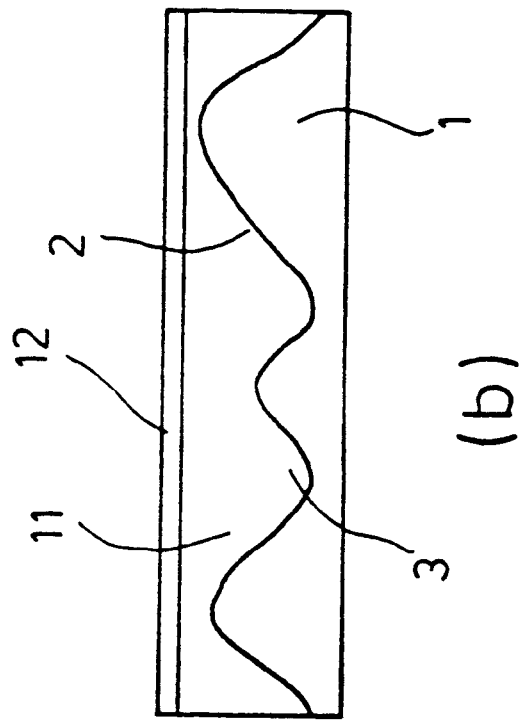
Figure 1:
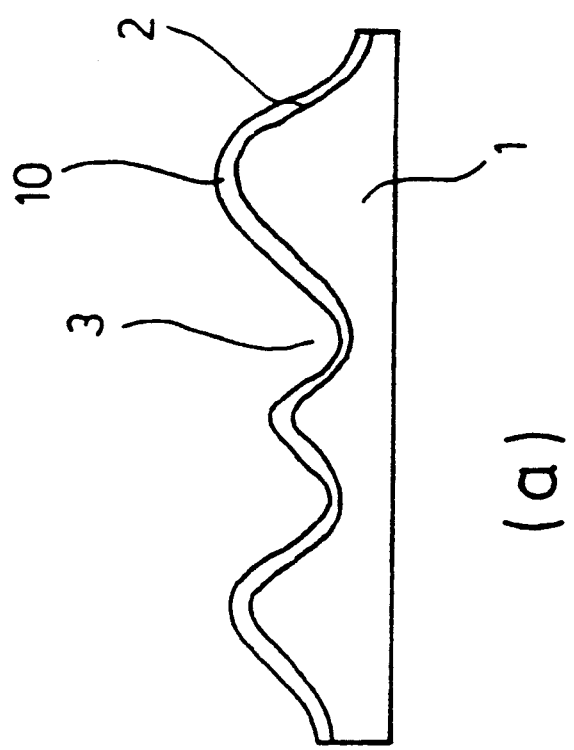

United States Patent
Walther et al.

[11] Patent Number: 5,985,355
[45] Date of Patent: Nov. 16, 1999

[54] PROCESS FOR COATING SURGICAL NEEDLES

[75] Inventors: Christoph Walther, Kattendorf; Gunther Raddatz, Hamburg, both of Germany

[73] Assignee: Ethicon, Inc., Somerville, N.J.

[21] Appl. No.: 09/037,942

[22] Filed: Mar. 10, 1998

[30] Foreign Application Priority Data

May 24, 1997 [DE] Germany .......................... 197 22 880

[51] Int. Cl.$^6$ .............................. B05D 1/38; B05D 3/02; B05D 5/08

[52] U.S. Cl. ................... 427/2.28; 427/379; 427/387; 427/409

[58] Field of Search .................................. 427/2.28, 2.1, 427/409, 384, 388.5, 379, 387

[56] References Cited

U.S. PATENT DOCUMENTS

| | | | |
|---|---|---|---|
| 2,814,296 | 11/1957 | Everett | 427/2.28 |
| 4,430,358 | 2/1984 | Wada | 427/2.28 |
| 4,720,521 | 1/1988 | Spielvogel et al. | 427/387 |
| 4,844,986 | 7/1989 | Karakelle et al. | 427/2.28 |
| 5,049,410 | 9/1991 | Johary et al. | 427/385.5 |
| 5,213,839 | 5/1993 | Awazu et al. | 427/2.28 |
| 5,258,013 | 11/1993 | Granger et al. | 427/427 |
| 5,266,359 | 11/1993 | Spielvogel et al. | 427/2.28 |
| 5,533,982 | 7/1996 | Rizk et al. | 604/239 |
| 5,534,609 | 7/1996 | Lewis et al. | 427/302 |
| 5,536,582 | 7/1996 | Prasad et al. | 427/387 |
| 5,736,251 | 4/1998 | Pinchuk | 427/387 |

*Primary Examiner*—Diana Dudash
*Attorney, Agent, or Firm*—Emil Richard Skula

[57] ABSTRACT

In a process for coating surgical needles, a leveling coat is applied to a surface of a surgical needle in one step or in several steps to fill in and/or level out surface roughness A slip coating is applied to the leveling coat

8 Claims, 2 Drawing Sheets

(a)

(b)

PROCESS FOR COATING SURGICAL NEEDLES

The invention relates to a process for coating surgical needles. The coating is intended to reduce the force (force of penetration) necessary to pass the surgical needles through tissue as compared with uncoated surgical needles (in particular with a metal surface).

A process is known from EP 0 494 648 A2 for preparing a siliconized surgical needle in which an amino alkyl siloxane is applied to the surface of the needle by immersion in a solution or by spraying and then cured at elevated temperature in order to produce a silicone coating. A product sold by Dow Corning under the name "MDX44159" is preferably used as amino alkyl siloxane, the heat treatment being carried out for half an hour or longer at ca 120° C.

In order to reduce the force of penetration, it is also known to immerse surgical needles in a solution of a condensable polymethyl siloxane in a mixture of n-heptane and xylene and then to remove the solvent by thermal after-treatment for one hour at 100° C. The product sold by Dow Coming under the name "Syl-Off DC 23", which exhibits an average degree of polymerization of ca 8000, is suitable as condensable polymethyl siloxane. If the surgical needle is provided with a bore which is intended to receive the end portion of a surgical thread, the bore should be filled with water prior to the surgical needle being immersed in the solution, so that the securing of the surgical thread is not impaired by the coating in the area of the bore.

The previously known processes admittedly produce surgical needles in which the force of penetration is clearly reduced compared with untreated needles. However, in these needles the force of penetration increases considerably when a tissue is pierced several times in succession with the same needle, as happens frequently in practice during operations.

It is the object of the invention to provide a process for coating surgical needles by means of which surgical needles can be produced in which the force of penetration is even less compared with surgical needles treated by previously known processes and in which the force of penetration does not increase as greatly after repeated penetration of tissue as in the case of the surgical needles coated by previously known processes.

This object is achieved by a process for coating surgical needles coated by the process of the present invention and by a surgical needle so coated.

In the process according to the invention for coating surgical needles, a leveling coat is applied to a (preferably metal) surface of a surgical needle in one step or in several steps to fill in and/or level out surface roughness, and a slip coating is applied to the leveling coat.

The surface roughness of the needle is greatly reduced by the leveling coat. The slip coating, acting as a lubricating film, is therefore situated on an essentially smooth substrate, which improves the of the slip coating. Even if the slip coating has more or less worn off after the needle has repeatedly penetrated tissue, the force of penetration increases to only a relatively small extent, which is attributed to the favorable interaction of the leveling coat and the slip coating. Therefore, the process according to the invention results in a favorable behavior of the surgical needles coated according to the process in the case of repeated penetration and in an improved penetration behavior of the needles.

In order to apply the leveling coat, the surgical needle is preferably immersed in a first solution containing a condensable polymethyl siloxane. The solvent located in the region of the needle is evaporated, and the condensable polymethyl siloxane is cured for a predetermined period at a predetermined temperature lying above room temperature. The heat treatment for curing the condensable polymethyl siloxane can be used simultaneously to evaporate the solvent located in the region of the needle. The described sequence of steps can, if desired, be repeated once or several times in order to build up a leveling coat with a greater layer thickness.

The cured, condensable polymethyl siloxane forms a mechanically stable film which fills in hollows in the surface of the surgical needle and is well suited as a base for the slip coating which is subsequently applied. The product sold by Dow Corning under the name "Syl-Off DC 23", which exhibits an average degree of polymerization of ca 8000, is preferably used as condensable polymethyl siloxane. "Syl-Off DC 23" has already been used for many years for coating surgical needles, and its application properties are considered acceptable at least in principle.

n-heptane or a mixture of n-heptane and xylene is suitable as solvent for the first solution. Being a non-polar solvent, it absorbs only very small quantities of water, which is advantageous if a bore, provided in the surgical needle and intended to receive the end portion of a surgical thread, is filled with water prior to the surgical needle being immersed in the first solution (see below).

In a preferred embodiment, the first solution is a solution of condensable polymethyl siloxane in n-heptane with added xylene, the condensable polymethyl siloxane being present in the concentration range of 10 g/l to 40 g/l. The quantities given relate here to the solids content (i.e. condensable polymethyl siloxane without solvent). In "Syl-Off DC 23" customary in the trade, a solids content of ca 30% to 33% is dissolved in xylene; the addition of xylene in the first solution is preferably due only to the xylene content of the used "Syl-Off DC 23" customary in the trade.

As a result of the large number of surgical needles to be coated, because of the small dimensions of the needles and because of their sensitivity to mechanical stress, it is particularly economical if the material provided for the leveling coat is brought to the surgical needles by immersion of the needles in the first solution The concentration range of the condensable polymethyl siloxane in n-heptane (preferably with added xylene) of 10 g/l to 40 g/l is particularly favorable The first solution has a relatively low viscosity in order to achieve a fast, trouble-free wetting of the needle surface and to be sure of preventing adjacent needles from sticking together. On the other hand, the concentration of the condensable polymethyl siloxane is high enough to bring a considerable quantity of material for the leveling coat to the surgical needles during an immersion process. In comparison, trouble-free coating of surgical needles with low layer thickness cannot be expected with plastic melts, owing to their high viscosities.

Curing of the condensable polymethyl siloxane preferably takes place for a period in the range of one hour to five hours at a temperature in the range of 130° C. to 250° C.

During curing, the condensable polymethyl siloxane is thermally crosslinked, whereby a mechanically stable, abrasion-free silicone film is obtained. According to information from the manufacturer (Dow Corning), a minimum temperature of 130° C. is necessary for thermal crosslinking of "Syl-Off DC 23". A temperature of 15° C. has proved to be particularly favorable for curing a leveling coat of "Syl-Off DC 23", but temperatures of e.g. 210° C. are also possible. The higher the temperature, the quicker the curing process. However, at too high temperatures, the silicone film may be discolored or destroyed by cracking.

As already mentioned, the temperature necessary for curing depends on the duration of the thermal treatment. The duration of the heat treatment must be long enough for the surface of the leveling coat to no longer be sticky at the end of the treatment.

A period of two hours for curing has proved to be particularly advantageous at a temperature of 150° C. The leveling coat is then no longer sticky and is stable over time.

Evaporation of the solvent located in the region of the needle preferably takes place at least partly at a temperature above room temperature. It is particularly advantageous to first allow the solvent to drip off and to air at room temperature after removal of the surgical needle from the first solution and then allow the leveling coat to cure, as already described. At the start of the curing process, the remains of the solvent which are still located in the region of the needle then evaporate at an elevated temperature. However, it is also conceivable to evaporate the solvent remains at a temperature above room temperature before the actual curing (e.g. at an even higher temperature) begins.

In a preferred embodiment of the process according to the invention, during the sequence of steps for applying the slip coating, the surgical needle provided with the leveling coat is immersed in a second solution which contains a polydimethyl siloxane having amino and alkoxy groups as functional groups. The solvent is then evaporated, preferably at a predetermined temperature above room temperature.

The slip coating acts as a lubricating film which considerably reduces the force of penetration of a coated needle. The polydimethyl siloxane sold by Dow Corning under the name "MDX4-4159" and having amino and alkoxy groups as functional groups has proved to be a particularly advantageous material for the slip coating. This material has been used for quite a long time already for coating surgical needles, and its application properties are therefore regarded as acceptable at least in principle. If the solvent evaporates at a predetermined temperature above room temperature, crosslinking or at least complete crosslinking of the slip coating is not sought, because this could result in an increase in the force of penetration.

The second solution preferably contains n-heptane as solvent. For the same reasons as for the first solution, it is advantageous to use a non-polar solvent and for example to do without constituents such as isopropanol or to use only a small addition of a polar solvent.

In a preferred embodiment, the second solution is a solution of 10 g/l to 50 g/l of polydimethyl siloxane having amino and alkoxy groups as functional groups in n-heptane, it also being possible to use an added polar solvent. The quantity given relates in this case to the solids content (i.e. polydimethyl siloxane without solvent). In "MDX4-4159" customary in the trade, a solids content of approximately 50% is dissolved in a mixture of aliphatic hydrocarbons and isopropanol; the addition of a polar solvent to the second solution is preferably due only to the isopropanol content of the used "MDX4-4159" customary in the trade. Analogously to the first solution, the concentration of the dissolved substance must not be too high, in order that the viscosity of the second solution is not too great and the surgical needles do not stick to each other.

Evaporation of the solvent of the second solution preferably takes place for a period in the range of 0.4 hours to 2.5 hours at a temperature in the range of 60° C. to 140° C. As already mentioned, thermal crosslinking of the slip coating is not sought particularly when "MDX4-4159" is used. In this case, a temperature of 100° C. certainly prevents a manually determinable stickiness of the surgical needle and does not result in a higher force of penetration than when the solvent of the second solution evaporates at room temperature. At a temperature of 100° C., a period of one hour for the evaporation of the solvent of the second solution has proved to be sufficient to avoid stickiness of the slip coating. It is also conceivable to allow the solvent of the second solution to evaporate at room temperature and not to use elevated temperatures.

At their end opposite the needle point, surgical needles of many types are provided with a bore which is intended to receive the end portion of a surgical thread. The inner wall of this bore should not come into contact with the material of the leveling coat or of the slip coating, in order that the adhesive capacity of adhesive by means of which the end portion of the surgical thread can be stuck on in the bore is not impaired. In order to achieve this, it is advantageous to fill the bore with water prior to the surgical needle being immersed in the first solution and/or prior to the surgical needle being immersed in the second solution.

When the bore is filled with water, a non-polar solution cannot enter the bore and wet its inner wall. A non-polar solution is present, for example, when n-heptane is used as the solvent.

The bore can be filled with water by exposing the surgical needle in a vessel containing distilled water to a below atmospheric pressure for a predetermined period. Under these conditions, the air originally present in the bore leaves the bore since it is under higher pressure.

If a wetting agent is added to the distilled water, entry of the distilled water into the bore is facilitated. For example, the product "Triton X 100 (0-[4-(1,1,3,3-tetramethylbutyl) phenyl]-deca(oxyethylene)), sold by Merck, is suitable as wetting agent.

If a wetting agent is used, the entrainment of substantial quantities of wetting agent into the first solution or into the second solution should be prevented. It is therefore advisable to rinse the surgical needle with distilled water after removal from the vessel containing distilled water and wetting agent and prior to immersion in the first solution or the second solution Distilled water still adhering to the needle after this does not interfere in the first solution or the second solution when a non-polar solvent such as n-heptane is used. In this case, the water carried in separates as a deposit with the result that the concentrations of the substances for the leveling coat and the slip coating in the first and second solution remain unchanged.

The invention is explained in more detail below with reference to examples.

The drawings show in

Figure 2:
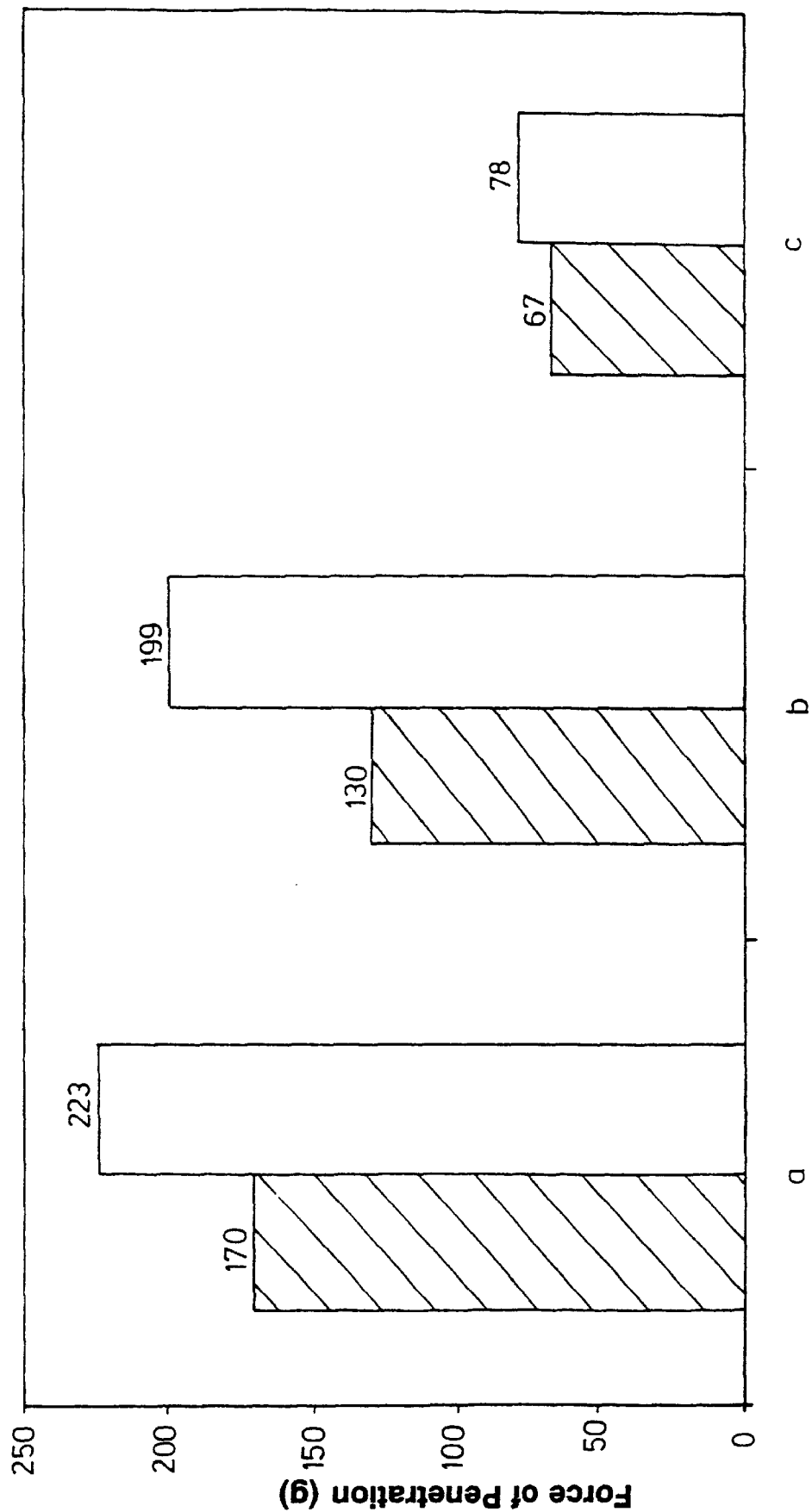

FIG. 1 a schematic view of the surface region of a surgical needle (a) coated in a conventional manner and of a surgical needle (b) coated in accordance with the process according to the invention, each in longitudinal section, and FIG. 2 a bar chart which illustrates the reduction in the force of penetration of needles (c) coated according to the invention compared with uncoated surgical needles (a) and surgical needles (b) coated according to a conventional process.

The sequence of the process according to the invention for coating surgical needles has already been explained in principle. FIG. 1 illustrates schematically how the surface of a needle looks after coating, in the left-hand part (a) after carrying out a conventional process and in the right-hand part (b) after carrying out the process according to the invention.

FIG. 1 shows a detailed view of a longitudinal section through a surgical needle 1 in the region of the surface 2. On a microscopic scale, the surface 2 is rough, i.e. it has bumps and hollows, such as hollow 3. The surgical needle 1 can be manufactured from any material suitable for surgical needles, in particular from metal materials.

In the left-hand part of FIG. 1, the coating 10 can be seen which was produced according to one of the conventional processes mentioned at the beginning. To that end, surgical needles having a metal clean surface were initially placed in distilled water with application of a below-atmospheric pressure in order to fill the bores at the ends of the needles opposite the needle points with distilled water, as already explained above. The needles were then immersed in a solution of "Syl-Off DC 23" in a mixture of n-heptane and xylene as solvent, the concentration being approximately 21 g/l (i.e. approximately 21 g of solids per liter of solvent). Following removal of the needles from the solution, excess solvent dripped off and partly evaporated at room temperature. The needles were then placed in a heating furnace, maintained at a temperature of 100° C., for one hour. During this time, the remaining solvent evaporated, whereas this temperature was not high enough at least for complete crosslinking of the "Syl-Off DC 23".

An examination under the microscope of a surgical needle coated according to this conventional process produces a picture as shown in the left-hand part (a) of FIG. 1. It can be seen that, although there is an unbroken coating 10 on the surface 2 of the needle 1, the hollows 3 are not filled in. Although the coating 10 does improve the penetration properties of the needle 1, the roughness still remains.

The right-hand part (b) of FIG. 1 shows a corresponding representation of a surgical needle coated according to the process described in detail in the following Example 1. In this case, the hollows 3 on the surface 2 ofthe needle I are filled in by a leveling coat 11 made of crosslinked "Syl-Off DC 23". Moreover, there is a slip coating (12) made of non-crosslinked "MDX4-4159".

Three examples of the process for coating surgical needles in accordance with the invention are explained in more detail below.

EXAMPLE 1

Metal round-bodied needles and cutting round-bodied needles having a diameter of 0.36 mm, 0.30 mm and 0.25 mm were coated in the manner described in detail below. These surgical needles were provided on the end opposite the needle point with a bore (to receive the end portion of a surgical thread). The needles were first immersed in a beaker in a 6% solution of the wetting agent "Triton X 100" (see above) in distilled water. The beaker containing the needles was placed in a vacuum flask and kept at a pressure of 0.1 bar (absolute) for approximately 30 minutes. By means of this treatment, the bores of the needles filled with the wetting agent solution. The needles were then taken from the beaker, and the wetting agent solution dripped off shortly.

In order to remove the wetting agent solution from the needle body, the needles were rinsed with distilled water in two steps immediately after the vacuum treatment. The first rinse took place at a water temperature of at least 60° C. with a rinsing period of at least one minute. The second rinse took place using water at room temperature and also lasted for at least one minute. After rinsing, the needles remained in the rinsing bath of the second rinse in order to prevent drying out of the bores.

Next, the needles were immersed in a sieve in a solution of "Syl-Off DC 23" (see above) in n-heptane, called "first solution" below. The concentration of the first solution was 21 g/l (i.e. 21 g of solids, deriving from "Syl-Off DC 23", per liter of solvent, i.e. n-heptane with added xylene, deriving from "Syl-Off DC 23"). The sieve was moved in the first solution to remove water adhering to the needles. The water did not mix with the n-heptane, but settled on the bottom of the bath with the first solution.

The needles were then poured out onto glassine paper and placed under a vent for at least 15 minutes to air.

In order to evaporate the remaining solvent located in the region of the needles and to cure the coating of "Syl-Off DC 23" formed on the needles, the needles were then treated in a heating furnace for a predetermined period of 120 minutes (±15 minutes) at a predetermined temperature of 150° C. (±5 K). A cooling phase took place for at least 15 minutes after removal from the heating furnace.

At the end of the sequence of steps described up to now, the needles had the lower layer of a leveling coat for filling in and/or leveling out the surface roughness of the metal needle surfaces.

In order to increase the layer thickness of the leveling coat, the sequence described previously was repeated in a second step using the same parameters. That is, the needles were again immersed in a 6% solution of "Triton X 100" in distilled water, rinsed with distilled water at 60° C. and at room temperature, immersed in the first solution (with the same composition as previously), dried and cured in the heating furnace at approximately 150° C. for approximately 2 hours and finally cooled to room temperature. The leveling coat then had the desired full thickness.

The subsequent sequence of steps for applying the slip coating began exactly like the respective sequences for applying the leveling coat: the needles were first immersed in the 6% solution of "Triton X 100" in distilled water with application of below-atmospheric pressure and then rinsed with distilled water at 60° C. and at room temperature, as described previously.

The needles were then immersed in a sieve in a bath containing a solution of "MDX4-4159" (see above) in n-heptane. The concentration of this solution, called "second solution", was 25 g/l (i.e. 25 g of solids, deriving from "MDX4-4159", per liter of solvent, i.e. n-heptane with addition of the solvents deriving from the commercial "MDX4-4159"). The sieve with the needles was moved in the bath with the solution to remove water adhering to the needles. The needles were then poured out onto glassine paper and placed under the vent for at least 15 minutes to air.

The needles were placed in the heating furnace for 60 minutes (±15 minutes) at a temperature of 100° C. (±5 K) in order to evaporate the remaining solvent. After removal from the heating furnace, a cooling phase took place for at least 15 minutes.

The process for coating the needles was thus complete, if desired, the needles could be demagnetized, visually checked, and subjected to a penetration test (for measurement of force of penetration, see below).

EXAMPLE 2

Surgical needles with a diameter of 0.20 mm and 0.15 mm were coated in a similar way to that described in Example 1. Unlike Example 1, the concentration of the first solution was only 13 g/l. Furthermore, the leveling coat was not applied in two sequences of steps, as in the first example, but in one single sequence, the treatment in the heating furnace again taking place for approximately 2 hours at approximately 150° C. Finally, the concentration of the second solution used for the slip coating was also less than in Example 1; it was 21 g/l. Evaporation of the remaining solvent took place as in Example 1 for ca 1 hour at ca 100° C.

EXAMPLE 3

In a further variant of the process for coating surgical needles, needles provided with a bore were first immersed in a basket in a vessel filled with distilled water and exposed to a below-atmospheric pressure of approximately 0.1 bar (absolute) in a vacuum flask for at least 30 seconds in order to fill the respective bore with water. The distilled water was dripped off shortly.

Next, to apply the leveling coat, the needles were immersed in a sieve in a first solution the composition of which was the same as that of the first solution from Example 1. The sieve was moved in the bath with the first solution to remove water adhering to the needles. The needles were then poured out onto glassine paper and placed under a vent for at least 15 minutes to air.

Unlike Examples 1 and 2, the residues of the first solvent were evaporated prior to curing the leveling coat. To that end, the needles were placed in a heating furnace for 60 minutes (±15 minutes) at a temperature of 100° C. (±5 K). After removal from the furnace, a phase for cooling to room temperature, at least 15 minutes in length, took place.

The curing of the leveling coat then took place in a heating furnace for a period of 2.5 hours (±15 minutes) at a temperature of 210° C. (±10 K). After removal from the heating furnace, a cooling phase of at least 15 minutes took place.

The leveling coat was applied in a single sequence of steps in this example, as in Example 2.

In order finally to produce the slip coating, after the respective bore had been filled with water (see above), the needles were immersed in a sieve in a second solution the composition of which was the same as that of the second solution of Example 1. The sieve was moved in the bath with the second solution in order to remove water adhering to the needles. The needles were then poured out onto glassine paper and kept under the vent for at least 15 minutes to air.

Finally, the remaining solvent of the second solution was evaporated in a heating furnace. To that end, the needles were placed in a heating furnace for 60 minutes (±15 minutes), the temperature of which was maintained at 100° C. (±5 K). After removal from the heating furnace, the needles were cooled to room temperature for at least 15 minutes.

The device described in U.S. Pat. No. 5,181,416, for example, can be used to examine the penetration properties of a surgical needle. Basically, the force necessary to guide the surgical needle through a test substance is measured. The force is greatest when the needle point pierces the test substance, it quickly diminishes as soon as a hole has been made through the test substance. When the rear part of the needle is drawn through the hole produced on piercing, the force is almost constant and, in the case of needles coated according to conventional processes, is typically approximately half as great as the force occurring when the test substance is pierced. When "force of penetration" is mentioned below, this means the force on drawing the needle through the test substance, that is after it has been pierced. This force of penetration is distinctly lower for needles coated in accordance with the process according to the invention than for conventionally coated or uncoated needles, whereas the forces necessary to pierce the test substance are approximately equal in both cases.

Suitable as test substance are for example silicone rubber or the artificial leather sold by Porvair under the name "Porvair", which is well comparable with solid, biological tissue in terms of penetration behavior.

FIG. 2 shows in the form of a bar chart the forces of penetration measured in the penetration test for a surgical needle of diameter 0.43 mm, (a) with an uncoated, metal-bright surface, (b) with a coating applied in one stage in accordance with a conventional process, as described in connection with part (a) of FIG. 1, and (c) with a coating applied according to the invention as in Example 1 explained above and consisting of a leveling coat and a slip coating.

"Porvair" with a thickness of 1.1 mm was used as test substance. The left-hand column in each case shows the force of penetration after the needle being used has pierced the test substance for the first time. The values given are average values from 25 individual measurements. The right-hand column in each case shows the force of penetration after the needle being used has pierced the test substance for the fifth time. The respective values are again average values from 25 individual measurements.

As FIG. 2 illustrates, the surgical needles coated in accordance with the process according to the invention not only have substantially lower forces of penetration than uncoated needles or needles coated in accordance with the conventional process when the test substance is pierced for the first time, but the needles coated according to the invention behave very favorably even after repeated penetrations. After five penetrations, a number typical in surgical operations, the force of penetration is only insignificantly above the value for the first penetration, completely in contrast to the uncoated surgical needles or those coated in accordance with the conventional process.

The conditions represented in FIG. 2 are typical. Evaluation of a large number of penetration tests using surgical needles of different shapes and different sizes, each coated in accordance with the conventional process and in accordance with the process according to the invention, revealed that the force of penetration in the case of the needles coated according to the invention is only approximately 50% to 80% of the force of penetration of the corresponding needles coated in accordance with the conventional process after the first penetration, and only approximately 30% to 70% thereof after the fifth penetration.

We claim:

1. A process for coating surgical needles, the process comprising the steps of:
 I. providing a surgical needle having a surface;
 II. forming a first leveling coating on the surface of the needle by the coating process comprising the steps of:
   applying a first coating solution to coat the surface of the surgical needle comprising condensable polymethyl siloxane and solvent;
   evaporating the solvent from the first coating solution; and,
   curing the coating for a sufficient period of time at a temperature above room temperature to effectively polymerize the polymethyl siloxane to form the leveling coating; and, III. forming a second slip coating over the leveling coating by a coating process comprising the steps of:

applying a second coating solution over the first coating, the second coating solution comprising polydimethyl siloxane having amino and alkoxy functional groups and solvent; and, evaporating the solvent from the second coating for a sufficient period of time and a sufficient temperature to effectively form the slip coating.

2. The process according to claim 1, characterized in that the solvent in the first solution comprises n-heptane.

3. The process according to claim 1, characterized in that the first solution comprises 10 g/l to 40 g/l of condensable polymethyl siloxane, n-neptane, and xylene.

4. The process according to claim 1, characterized in that curing takes place for a period in the range of 1 hour to 5 hours at a temperature in the range of 130° C. to 250° C.

5. The process according to claim 1, characterized in that evaporation of the solvent from the first coating takes place at least partly at a temperature lying above room temperature.

6. The process according to claim 1, characterized in that the solvent in the second coating solution comprises n-heptane.

7. The process according to claim 1, characterized in that the second coating solution comprises 10 g/l to 50 g/l of polydimethyl siloxane having amino and alkoxy groups as functional groups, n-heptane, and a polar solvent.

8. The process according to claim 1, characterized in that at least part of the evaporation of the solvent from the second coating solution takes place for a period in the range of 0.4 hours to 2.5 hours at a temperature in the range of 60° C. to 140° C.

* * * * *